United States Patent
Dunfee et al.

(10) Patent No.: US 9,423,803 B2
(45) Date of Patent: Aug. 23, 2016

(54) METHODS, SYSTEMS, AND APPARATUS PROVIDING TEMPERATURE-CONTROLLED PROCESS FLUID

(75) Inventors: William D. Dunfee, Newark, DE (US); Robert E. Myers, Lewes, DE (US); Lawrence D. Huppman, Middletown, DE (US); Nathan A. Small, Bear, DE (US); John P. Mizzer, Newark, DE (US); Richard H. Carter, Jr., Merion Station, PA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 778 days.

(21) Appl. No.: 13/810,381
(22) PCT Filed: Jul. 8, 2011
(86) PCT No.: PCT/US2011/043315
§ 371 (c)(1), (2), (4) Date: Jan. 15, 2013
(87) PCT Pub. No.: WO2012/009213
PCT Pub. Date: Jan. 19, 2012

(65) Prior Publication Data
US 2013/0112761 A1     May 9, 2013

Related U.S. Application Data

(60) Provisional application No. 61/364,629, filed on Jul. 15, 2010.

(51) Int. Cl.
*B01L 7/00* (2006.01)
*F28D 20/00* (2006.01)
(Continued)

(52) U.S. Cl.
CPC .............. *G05D 23/1306* (2013.01); *B01L 7/00* (2013.01); *F24H 1/12* (2013.01); *F24H 9/2007* (2013.01);
(Continued)

(58) Field of Classification Search
CPC .......... G05D 23/1306; F24H 1/10; F24H 1/12; F24H 24/0072; F24H 24/12; F24H 24/2007; F24H 24/14; F24H 24/146; F16K 49/00; F16K 49/005; F16K 49/007; F16K 53/00; F16K 53/001; F16L 53/00; F16L 53/001; F28D 20/00; F28D 2020/0065; F28D 2020/0069; F28D 2020/0078; F28D 21/00; F28D 2021/005; F28D 2021/0019; B01L 7/00; G01N 35/00; G01N 35/1016; G01N 2035/0346; G01N 1/44; Y10T 37/0329; Y10T 37/6416; Y10T 37/6552; Y10T 37/6579; Y10T 37/8766
USPC ............ 137/334, 340; 165/96, 100, 103, 108, 165/138; 210/175, 184; 73/863.11; 422/500, 501, 530, 537

See application file for complete search history.

(56) References Cited

U.S. PATENT DOCUMENTS 2,417,950 A * 3/1947 Rothwell .............. E03C 1/0411
                                                    137/340
2,441,361 A * 5/1948 Kirgan ................. B01D 1/0082
                                                    159/24.3

(Continued)

*Primary Examiner* — Joseph Drodge

(57) ABSTRACT

Disclosed are systems and apparatus adapted to control a temperature of a process fluid in an instrument. In one aspect, the systems and apparatus are adapted to control fluid temperature provided to a feed tank. The feed tank may feed a metering system and metering line of an instrument such as a clinical analyzer. The fluid temperature control system includes a process fluid inflow, a process fluid outflow, a first fluid path fluidly coupled to the process fluid inflow and outflow, and at least one heat exchanger thermally coupled to the first fluid path, wherein the heat exchanger is adapted to extract heat for at least one heat-generating component of the instrument. Controlling a temperature of the process fluid at the feed tank improves metering accuracy. Methods of operating the system are provided, as are other aspects.

22 Claims, 10 Drawing Sheets

(51) Int. Cl.
*F28D 21/00* (2006.01)
*G01N 35/00* (2006.01)
*F24H 1/12* (2006.01)
*G01N 1/44* (2006.01)
*G05D 23/13* (2006.01)
*G01N 35/10* (2006.01)
*F24H 9/20* (2006.01)

(52) U.S. Cl.
CPC .............. *G01N 1/44* (2013.01); *G01N 35/1016* (2013.01); *F28D 2021/0019* (2013.01); *Y10T 137/0329* (2015.04); *Y10T 137/6579* (2015.04); *Y10T 137/8766* (2015.04)

(56) References Cited

U.S. PATENT DOCUMENTS

| | | | | |
|---|---|---|---|---|
| 2,876,182 | A * | 3/1959 | Hopper | B01D 9/0022 159/45 |
| 4,674,876 | A * | 6/1987 | Rossiter | 356/244 |
| 5,203,496 | A * | 4/1993 | Kline | G05D 23/1346 137/896 |
| 5,345,079 | A * | 9/1994 | French et al. | 250/288 |
| 6,002,475 | A * | 12/1999 | Boyd et al. | 356/246 |
| 6,324,865 | B1 | 12/2001 | Lee et al. | |
| 6,413,233 | B1 | 7/2002 | Sites et al. | |
| 6,701,774 | B2 | 3/2004 | Srinivasan et al. | |
| 6,928,311 | B1 * | 8/2005 | Pawluczyk et al. | 600/310 |
| 7,037,430 | B2 * | 5/2006 | Donaldson et al. | 210/652 |
| 7,347,057 | B1 * | 3/2008 | Garrabrant et al. | 62/148 |
| 7,947,240 | B2 * | 5/2011 | Vandor | 423/225 |
| 8,794,002 | B2 * | 8/2014 | Held et al. | 60/651 |
| 8,875,513 | B2 * | 11/2014 | Paya Diaz | 60/641.6 |
| 2002/0050478 | A1 * | 5/2002 | Talbert | C02F 1/02 210/742 |
| 2003/0000213 | A1 * | 1/2003 | Christensen et al. | 60/670 |
| 2005/0037485 | A1 * | 2/2005 | Rodgers et al. | 435/287.2 |
| 2008/0058697 | A1 | 3/2008 | Kamen et al. | |
| 2009/0220966 | A1 | 9/2009 | Stanley et al. | |
| 2010/0066374 | A1 | 3/2010 | Trygstad et al. | |
| 2010/0315083 | A1 * | 12/2010 | Pauli et al. | 324/309 |

\* cited by examiner

METHODS, SYSTEMS, AND APPARATUS PROVIDING TEMPERATURE-CONTROLLED PROCESS FLUID

RELATED APPLICATIONS

The present application claims priority to U.S. Provisional Patent Application Ser. No. 61/364,629, filed Jul. 15, 2010, and entitled "METHODS, SYSTEMS, AND APPARATUS PROVIDING TEMPERATURE-CONTROLLED PROCESS FLUID,", which is hereby incorporated herein by reference in its entirety for all purposes.

FIELD OF THE INVENTION

The present invention relates generally to methods, systems, and apparatus adapted to provide a temperature-controlled process fluid.

BACKGROUND OF THE INVENTION

In medical specimen testing, purified water may be dispensed for various purposes. In certain clinical analyzer instruments used to test for the presence of an analyte in a bio-fluid sample (otherwise referred to as "specimens"), it may be desirable to precisely meter water to be used in the process. For example, in some automated testing systems (e.g., clinical analyzer instruments), specimens contained in sample containers (such as test tubes, sample cups, vials, cuvettes, and the like) may be tested to determine a presence of a particular analyte or substance contained therein. As part of this process, precise metering of a process fluid (e.g., purified water) may be desired. In order to provide for testing accuracy, such metering should be relatively precise.

For example, in some testing methods, such as the so-called "chase method," a volume of sample fluid is first aspirated and dispensed by a metering apparatus, and the dispensing of this sample fluid is followed (chased) by dispensing a precisely-metered volume of a process fluid (e.g., purified water). In the chase method, the volume of dispensed process fluid may be greater than the volume of the sample fluid that is dispensed. In the so-called "neat method," a small amount of sample fluid is aspirated and dispensed (on the order of 1-3 µL). In the neat method, the process fluid itself (e.g., purified water) may be the vehicle that allows for the metering of the sample fluid, even though the process fluid is not itself dispensed in the neat method. However, for both methods, it should be understood that inaccurate metering may lead to errors in specimen testing.

Accordingly, methods, systems, and apparatus that may improve accuracy of metering of a process fluid (e.g., purified water) are desired.

SUMMARY OF THE INVENTION

According to a first aspect, an improved instrument fluid temperature control system is provided. The system includes a process fluid inflow of the instrument adapted to provide a process fluid; a process fluid outflow of the instrument; a first fluid path fluidly coupled to the process fluid inflow and the process fluid outflow; and at least one heat exchanger coupled to the first fluid path and adapted to extract heat generated by the instrument and heat the process fluid.

In a method aspect, an improved method of providing a temperature-controlled process fluid in an instrument is provided. The method includes providing a process fluid inflow of the instrument; providing a process fluid outflow of the instrument; flowing process fluid from the process fluid inflow into a first fluid path that is fluidly coupled to the process fluid outflow; flowing the process fluid through at least one heat exchanger thermally coupled to the first fluid path to extract heat from one or more heat-generating components of the instrument and provide a heated process fluid; and flowing the heated process fluid to the process fluid outflow.

In another method aspect, an improved method of providing a temperature-controlled process fluid is provided. The method includes providing a temperature-controlled feed tank; providing a metering system fluidly coupled to the temperature-controlled feed tank; providing a probe fluidly coupled to the metering system by a metering line; and flowing the process fluid through the metering line, wherein a temperature of the process fluid contained in the temperature-controlled feed tank is controlled to about +/−20% (in ° C.) from a nominal operating temperature causing aspiration accuracy, dispensing accuracy, or both to be improved.

In an apparatus aspect, a fluid temperature control apparatus is provided. The apparatus includes a fluid temperature control apparatus of an instrument, comprising: a process fluid inflow; a process fluid outflow; a fluid purifier coupled to the process fluid outflow; a first fluid path fluidly coupled to the process fluid inflow and process fluid outflow; a first heat exchanger thermally coupled to the first fluid path; a second heat exchanger thermally coupled to the first fluid path and adapted to extract heat from at least one heat-generating component of the instrument; and a second fluid path fluidly coupled to an outflow of the fluid purifier and the first heat exchanger.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and descriptions are to be regarded as illustrative in nature, and not as restrictive. The drawings are not necessarily drawn to scale. The invention is to cover all modifications, equivalents, and alternatives falling within the spirit and scope of the invention.

DETAILED DESCRIPTION

For at least the above-described reasons, achieving precision in the metering of a process fluid in medical specimen testing is desirable. It has been discovered by the inventors that a substantial part of a metering error in some metering systems may be attributed to changes in a temperature of the process fluid contained within a metering line extending between a metering pump and a probe (e.g., sample probe). In particular, the inventors herein have discovered that variations in a temperature of the process fluid (e.g., purified water) contained in the metering line over time may affect a volume of the process fluid dispensed. Additionally, in cases where a secondary fluid is dispensed (e.g., a bio-fluid sample such as blood, serum/plasma, urine, interstitial fluid, etc.) but where the process fluid is fluidly coupled to the secondary fluid, it was discovered that the expansion or contraction of the process fluid in the metering line may likewise appreciably affect the precision of metering of the secondary fluid. For example, if a specimen drawn from a sample fluid to be tested is provided at the probe end and is only present therein for a short period of time, it is therefore not appreciably subject to such temperature variations. However, because the process fluid may be contained in the metering line for a relatively longer period of time, it is subject to temperature variations over time. Accordingly, volumetric expansion and contraction of the process fluid contained in the metering line due to temperature variations over time may contribute to aspiration and/or dispensing inaccuracies, and, therefore, may contribute to testing inaccuracies.

In some instances, such as those where the metered volume of the sample fluid is quite small (such as in the above-mentioned "neat method"), the contribution of fluid expansion and/or contraction of the process fluid over time may significantly affect overall testing accuracy.

Figure 1A:
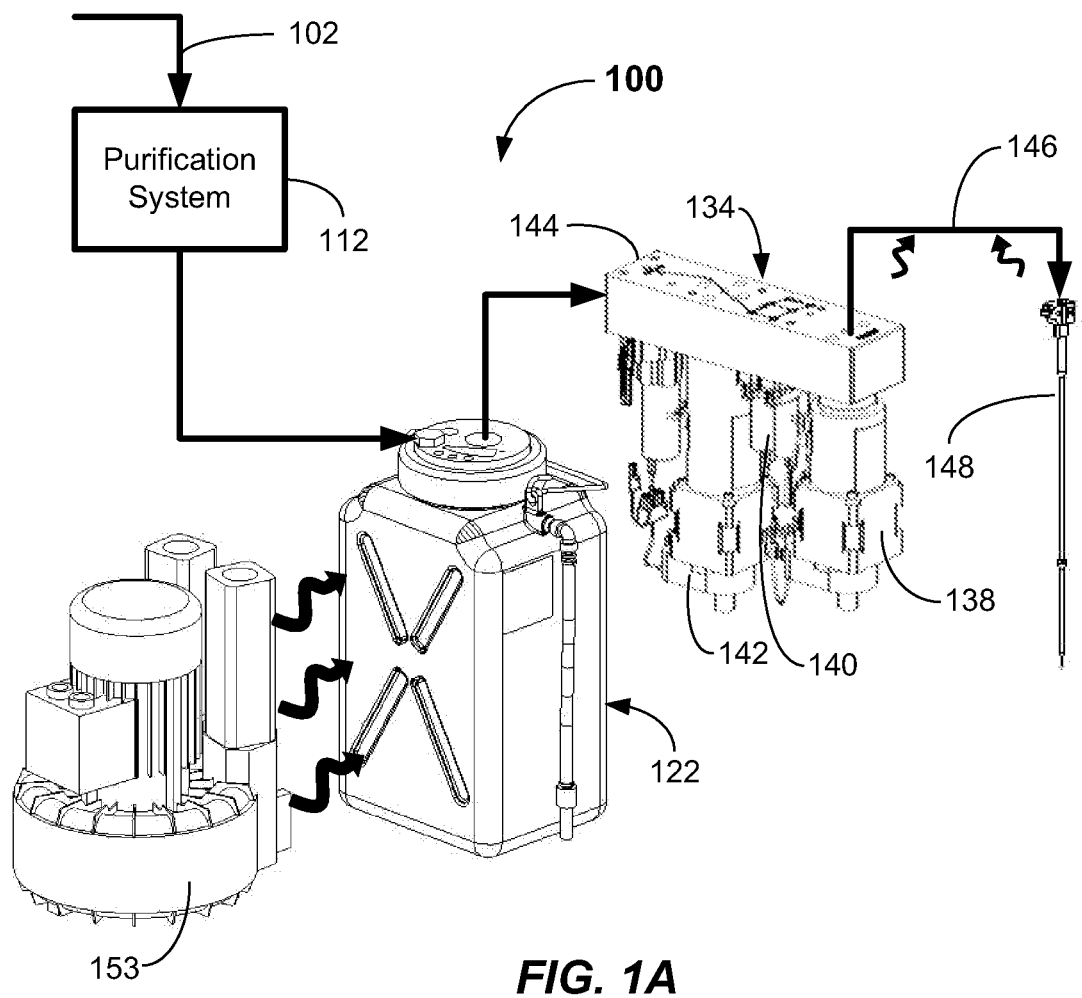
FIG. 1A is a perspective illustration of an exemplary process fluid metering system according to the Prior Art.

As shown in FIG. 1A, a prior art testing system 100 includes a feed tank 122, which provides a supply of purified water to a fluid metering apparatus 134 including a metering pump 138, valves 140, flush pump 142, and a distribution manifold 144, metering line 146, and probe 148. The metering line 146 fluidly couples the probe 148 (for aspirating and dispensing fluids) to the distribution manifold 144. The feed tank 122 in the prior art testing system 100 is filled directly from a purification system 112, which receives its inflow of process fluid (e.g., water) directly from a water supply 102.

Temperature variations experienced in the metering line 146 may come from multiple sources. For example, in some instances, steady use may contribute to temperature variations (e.g., temperature increases over time), which may arise from heat being transferred by convection, conduction, and/or radiation from other system components, such as the vacuum pump 153 shown. Additional temperature variations may come from intermittent filling of the tank with relatively cooler water from the purification system 112. This is especially true at times of high usage of the testing system 100. Other contributors may be due to changes in temperature of the water supply 102 (e.g., daily or seasonal changes in water supply temperature), starting and stopping the testing system 100, and changes in ambient temperature to which the testing system 100 is exposed.

Figure 1B:
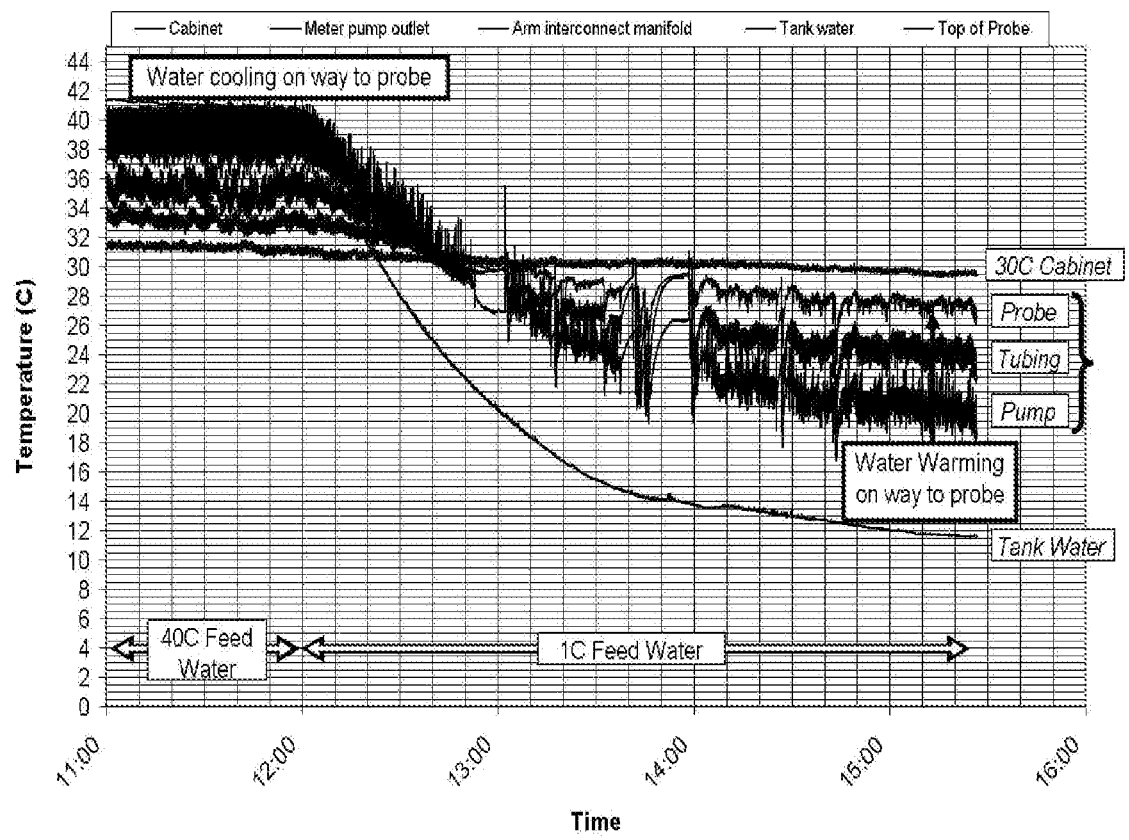
FIG. 1B is a plot illustrating temperature vs. time for various metering system components.

For example, as shown in FIG. 1B, variations in temperature of the inflow water from the water supply 102 provided to the purification system 112 produce temperature variations at the feed tank (Tank Water), at the metering pump 138 (Pump), at the probe 148 (Probe), and in the metering line 146 (Tubing) over time. Such temperature changes experienced due to changes in the inflow water temperature may result in contraction and/or expansion of the process fluid (e.g., purified water) contained in the metering line 146. As stated, this relative change in fluid volume in the metering line 146 may affect metering accuracy over time. Accordingly, inaccuracies in metering may lead to inaccuracies in the testing results.

In view of the foregoing problems, the present invention in one aspect provides methods, systems, and apparatus adapted to control a temperature of the process fluid in the metering line. In particular, it is desired to control the temperature in the metering line to vary by no more than about +/−20% from a nominal operating temperature. According to aspects of the invention, in some instances, this may involve controlling an outflow temperature of the process fluid provided to the metering line from a feed tank, which is adapted to provide a reservoir of purified water ready for use by the metering system. Controlling a temperature of the process fluid at the feed tank resultantly controls the temperature of the process fluid in the feed line coupled thereto.

According to another aspect, the invention is a method and system for recycling heat from waste water produced by a purifier (e.g., a purification system). At least some of the recycled heat may be extracted and used to preheat the process fluid provided to the purification system. Accordingly, energy costs are reduced and a temperature of the process fluid in the feed tank and provided to the metering line may be relatively stabilized.

These and other aspects and features of the invention will be described with reference to FIGS. 2-11 herein.

Figure 2:
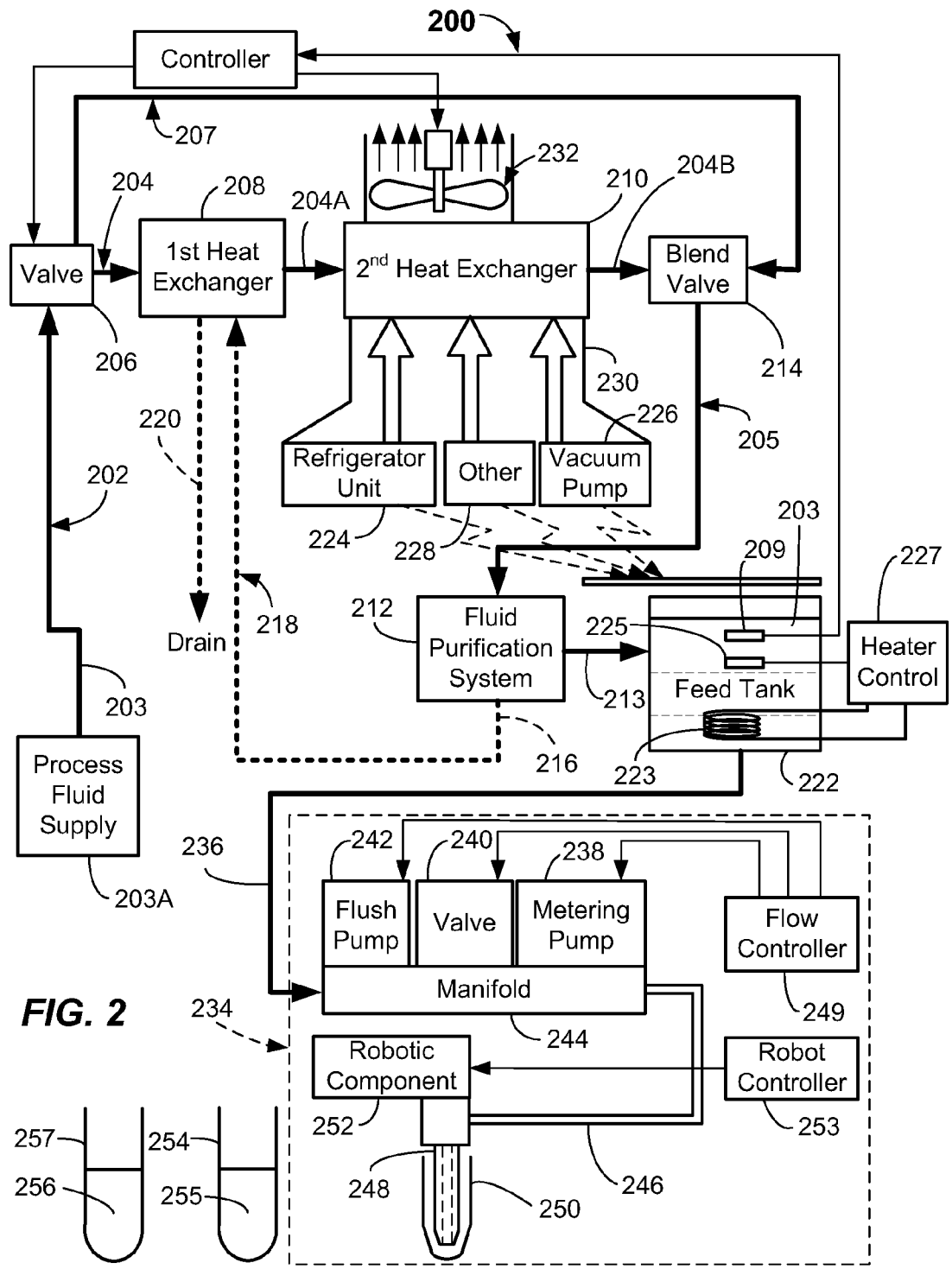
FIG. 2 is a block diagram illustration of a fluid temperature control system according to an aspect of the present invention.

In accordance with a first embodiment of the invention, as best shown in FIG. 2, a process fluid temperature control system 200 of an instrument is described. The process fluid temperature control system 200 may be coupled to, or be part of, a precision metering system 234 of the instrument. The instrument may be a clinical analyzer, for example. The process fluid temperature control system may be provided in other systems in which precisely controlled fluid temperatures are desired. The process fluid inflow 202 receives a flow of a process fluid 203 (e.g., water) for the process fluid temperature control system 200 from a process fluid supply 203A. The process fluid inflow 202 may be fluidly connected and coupled to a first fluid path 204, which in the depicted embodiment is fluidly coupled to a process fluid outflow 205. The first fluid path 204 may include at least one heat exchanger therein. In the depicted embodiment, more than one heat exchanger is included, such as a first heat exchanger 208 and a second heat exchanger 210, which may be provided in serial connection. However, the first heat exchanger 208 is optional. The process fluid inflow 202 of process fluid 203 into the process fluid temperature control system 200 may be controlled via a valve 206, such as any suitable valve (e.g., a solenoid valve). Other types of valves may be used. The valve 206 may be positioned at any suitable position to control inflow 202 of the process fluid 203 into the first fluid path 204 and also to a bypass path 207. At times, the fluid flow in bypass path 207 may be blended with a flow of a heated process fluid 203 from the first fluid path 204 to provide a heated and temperature-controlled process fluid 203 in the fluid outflow 205.

As process fluid 203 is used by the instrument, process fluid 203 needs to be replenished in the process fluid temperature control system 200. As dictated by a level sensor 209 (e.g., a float type sensor) situated at an appropriate level in a feed tank 222, the valve 206 may be opened and a fresh supply of process fluid 203 may be allowed to enter into the system 200. The process fluid 203 may be used, for example, in the metering system 234 (shown dotted) coupled to the fluid temperature control system 200. The process fluid 203 is preferably water. However, other process fluids may be used.

The process fluid temperature control system 200 may further include a fluid purifier such as purification system 212 fluidly coupled to the process fluid outflow 205. The purification system 212 may be any system, which operates to filter and/or otherwise purify the process fluid 203 so as to provide purified process fluid (e.g., water) in the instrument. The purification system 212 may include pretreatment devices, a reverse osmosis device, UV ionization, polishing, degassing, one or more particulate filters, and/or other conventional devices and/or treatments for filtering and/or purifying the process fluid 203 (e.g., water) to a relatively high level of purity. For example, the purification system 212 may remove organics, minerals, particles or sediment, dissolved oxygen, or other contaminants from the process fluid 203. The purified process fluid (e.g., water) may be used to dilute fluid samples, prepare reagents (e.g., where the process fluid 203 is added to a solid or powdered reagent material), dispense and/or aspirate liquid reagents (e.g., concentrated reagents), aspirate or dispense specimens, wash sample containers, and/or clean probes, for example. The purification system 212 may also include various conduits, valves, accumulators, and other components. The purification level of the process fluid may be to ASTM/NCCLS standards (e.g., NCCLS—National Committee on Clinical Laboratory Standards). For example, the process fluid 203 may be purified to a level that is suitable for dispensing in a metering system 234 adapted to be used for aspiration and/or dispensing in the testing of analytes or other substances in a bio-fluid (blood, plasma and/or serum, urine, cerebral fluid, etc.). For example, the purity may be sufficient to meet the standards for ASTM/NCCLS Type 1-IV and/or Type A-C, for example. Preferably, ASTM/NCCLS Type 1 and Type A purity standards may be provided by the purification system.

In the purification process carried out by the purification system 212, only a fraction of the process fluid 203 is purified and flows to the feed tank 222. That purified fraction is provided in feed line 213 (e.g., a conduit) to the feed tank 222. Valves, such as check valves, may be provided therein (not shown). The remaining waste fluid fraction may exit in an outflow conduit 216 and may be provided in a second fluid path 218.

The waste fluid in the second fluid path 218 may pass through the first heat exchanger 208 and then exit in an outflow conduit 220 from the first heat exchanger 208. The outflow conduit 220 may be provided to a drain, such as when the process fluid 203 is water. Waste heat from the waste fluid flowing in the second fluid path 218 from the purification system 212 is thermally transferred to the process fluid 203 passing through the first heat exchanger 208 in the first fluid path 204. The heat transfer may be through at least conduction (but possibly convection and radiation also) thereby, to the extent waste heat is available, preheating the process fluid 203 flowing from the heat exchanger 208 in path segment 204A. The extraction and use of the waste heat by the first heat exchanger 208 reduces the overall power requirements of the system 200 to heat the process fluid 203.

The first heat exchanger 208 may be any suitable type of heat exchanger, such as a liquid-to-liquid heat exchanger. An example of a liquid-to-liquid heat exchanger is a plate heat exchanger shown in FIG. 3. The first heat exchanger 208 may include a plurality of parallel conductive plates 310 thermally coupled to the fluid paths 204, 218. The flow of the paths 204, 218 may be counter flow, and the first heat exchanger 208 may include multiple counter flow passes for each fluid path 204, 218. Other types of heat exchangers may be employed.

Again referring to FIG. 2, heat (depicted by solid arrows) from one or more components of the instrument, such as refrigerator unit 224, vacuum pump 226, and/or other components 228 may be extracted and provided to the second heat exchanger 210. One or more shrouds 230 may be provided that at least partially surround or provide a confined air fluid path from the one or more components 224, 226, 228. A fan 232 may be operated to draw air across the one or more components 224, 226, 228 and through the second heat exchanger 210. This air flow functions to transfer heat via conduction, convection, and/or radiation from the one or more components 224, 226, 228 to the process fluid 203 contained in the first fluid path 204. As such, the process fluid 203 in the outflow segment 204B may be relatively heated as compared to its inflow temperature.

Figure 4:
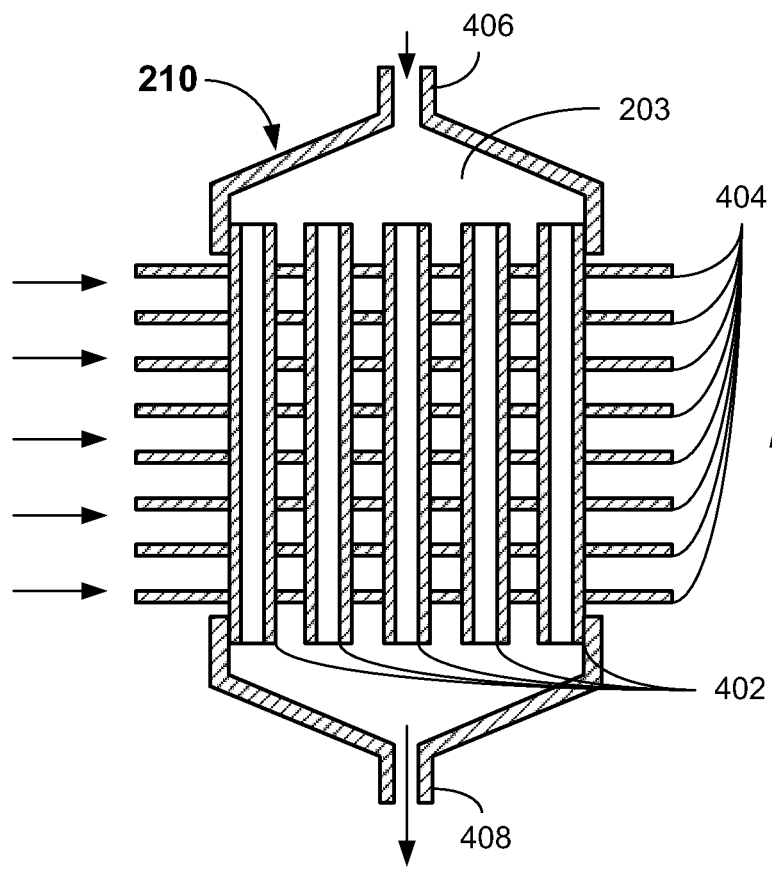
FIG. 4 is a cross sectioned side view illustration of an exemplary air-to-liquid heat exchanger according to embodiments of the present invention.

In the depicted embodiment, the second heat exchanger 210 may be an air-to-liquid type heat exchanger, such as a tube and fin heat exchanger as depicted in FIG. 4. The heat exchanger 210 may include a plurality of cross flow tubes 402, which may be surrounded by, and in thermal contact with, a plurality of fins 404. The process fluid 203 flows through the exchanger 210 from the inlet 406 to the outlet 408 as shown. Heat from the one or more components 224, 226, 228 is transferred to the process fluid 203 by flowing the heated air across the fins 404. This exchanges heat to the cross flow tubes 402. Other heat exchanger types may be used as well as other tube and fin configurations. For example, the process fluid 203 may pass through the second heat exchanger 210 in a conduit having multiple serpentine paths provided in thermal contact with the fins and tubes such that heat is transferred into the process fluid 203 (See FIG. 10). First and second heat exchangers 208, 210 may be provided in any order. Furthermore, the second heat exchanger 210 may be a liquid-to-liquid heat exchanger if the one or more components 224, 226, 228 of the instrument were to be liquid cooled.

Again referring to FIG. 2, in a preferred implementation, a temperature of the process fluid 203 in the feed tank 222 is maintained at a relatively constant temperature. For example, the temperature may be maintained and controlled to be about +/−20% as measured in degrees Celsius from a nominal operating temperature, or even about +/−15%, or even about +/−10% from a nominal operating temperature measured in ° C. In some embodiments, the process fluid temperature in the feed tank 222 is controlled to be about 30° C.+/− about 5° C., or even about 30° C.+/− about 3° C. Other controlled temperatures may be used.

In the present invention, a blend valve 214 may be used to precisely control a temperature of the process fluid 203 in the process fluid outflow 205. Accordingly, precisely heated process fluid 203 may be provided to the purification system 212. The blend valve 214 may include an integral or associated temperature sensor or thermostat adapted aid in the process of blending heated process fluid from the first fluid path 204 and unheated process fluid in the bypass path 207. The blend valve 214 is adapted to blend the differing temperature fluids 203 in the fluid paths 204, 207 in a desired ratio to arrive at a desired (predetermined or preset) temperature of the heated process fluid 203 in the process fluid outflow 205. This temperature set point may be set manually, or may be controlled by a processor responsive to a temperature sensor output.

To the extent that the temperature of the process fluid 203 in feed line 213 may be insufficient to heat the process fluid 203 to a desired temperature, an optional auxiliary heater 223 may be provided in the feed tank 222 or elsewhere (e.g., around the feed line 213). A temperature sensor 225 may operate with a heater control 227 to monitor and heat the process fluid 203 in the feed tank 222 to the desired set point. To the extent that sufficient heat is being provided from the heat exchangers 208, 210, the auxiliary heater 223 may be inoperative. However, in instances of high usage or initial startup, where fresh supply of process fluid 203 is constantly being provided to the process fluid temperature control system 200 or where the process fluid temperature control system 200 has been shut down and has equilibrated with ambient conditions, some initial auxiliary heating may be desired.

In the exemplary process fluid temperature control system depicted, a metering system 234 may be fluidly coupled to the process fluid outflow 205. For example, the coupling may through the fluid purification system 212 and the feed tank 222 of the process fluid temperature control system 200. The feed tank 222 may be fluidly couple to the metering system 234 by feed conduit 236. The metering system 234 (shown dotted) may be adapted to meter (dispense) a precise amount of the heated process fluid 203 or otherwise aspirate or dispense a fluid sample by using the process fluid 203 as the vehicle for doing so. The process fluid 203 may be used in a process for determining an amount of an analyte or other component in a fluid sample (e.g., a bio-fluid sample), for example. The metering system 234 may include a metering pump 238, and may also include one or more valves 240, a flush pump 242, and/or a distribution manifold 244. A metering line 246 may be fluidly connected to and between the metering pump 238 and a probe 248 (e.g., a sample probe). The probe 248 may include a hollow channel (shown dotted), which is adapted to aspirate and/or dispense a sample fluid, liquid reagent, and/or dispense the heated process fluid 203. The metering line 246 may be fluidly connected to the metering pump 238 by valve 240 and distribution manifold 244. In the depicted embodiment, the flow control of heated process fluid 203 to the metering line 246 may be through control of one or more control valves 240 and operation of the metering pump 238 by suitable control signals from a flow controller 249.

In the process of metering the heated process fluid 203, the one or more valves 240 are opened and the metering pump 238 may be activated via suitable control signals from flow controller 249 to allow flow of the heated process fluid 203 to the metering line 246. This may provide a relatively more precise volume of metered process fluid 203 in the metering line 246 to the probe 248. At various points in the testing process, fluid flushing of the probe 248 may be accomplished to clean sample fluid and/or reagent or other testing fluids from the probe 248. The flushing may be accomplished via a control signal from the flow controller 249 to the one or more valves 240 and the flush pump 242 causing the opening of the one or more valves 240 to allow a connection to the metering line 246 through distribution manifold 244. Flushing involves a rapid flow of the process fluid 203 for cleaning purposes and, thus, the flush pump 242 need not be capable of precise metering.

In the case of the metering pump 238, it should be capable of precisely metering process fluid 203 with relatively high accuracy in either a dispensing mode and/or an aspirating mode. For example, the metering pump 238 should be able to meter to a volumetric accuracy of at least about +/−0.02 µL or less. The distribution manifold 244 may include a plurality of internal fluid paths fluidly connecting the flush pump 242 and metering pump 238 through valve 240 to the metering line 246 and feed conduit 236.

In one operational method according to an aspect of the invention, the sample probe 248 is used to dispense a sample and/or process fluid 203. For example, in the above-mentioned "chase method," a robotic component 252 operable based upon control signals from a robotic controller 253 may position the probe 248 into a sample container 254 containing a volume of sample fluid 255 (e.g., blood or a blood component). The metering pump 238 may then draw (aspirate) a small volume of the sample fluid 255 (e.g., 5 µL) into the channel of the sample probe 248 from the sample container 254 via appropriate signals from the flow controller 249, move the probe 248 via operation of the robotic component 252 and transfer (dispense) at least some of that small amount of the sample fluid 255 to a test container 250 (e.g., a cuvette). During the act of dispensing, the heated process fluid 203 is fluidly coupled to, and in contact with, the sample fluid 255 contained in a probe 248. Operation of the metering pump 238 causes flow of the heated process fluid 203 in the metering line 246 and thus flow of sample fluid 255 fluidly coupled thereto and abutting therewith. This sample dispensing may be chased by operating the metering pump 238 and dispensing a volume of the process fluid 203 through the metering line 246 from the probe 248 into the test container 250. The probe 248 (or a different probe and metering system utilizing the process fluid 203 as a liquid vehicle) may also aspirate and dispense liquid reagent 256 from a reagent container 257 as needed for the testing operation. Operation of the metering pump 238 causes flow of the heated process fluid 203 in the metering line 246 and, thus, flow of liquid reagent 256 fluidly coupled thereto and abutting therewith. Accordingly, dispensing accuracy when dispensing/aspirating liquid reagent 256 may also be improved. It should be apparent that the present inventive process fluid temperature control system 200 may be coupled to, and provide heated process fluid 203 to one, or more than one metering system (e.g., metering system 234).

The temperature of the process fluid 203 in the feed tank 222, and thus in the metering line 246, is temperature controlled as discussed above. In some embodiments, the chasing of the sample fluid 255 with the heated process fluid 203 involves dispensing a relatively larger volume of the process fluid 203 (e.g., 20 µL) than the volume of the sample fluid 255, thereby mixing the sample fluid 255 and the heated process fluid 203 in the test container 250. Thus, it should be understood that in some embodiments, the invention allows the precise metering of a temperature-controlled process fluid 203. In others, precise metering of the sample fluid 255 only is accomplished (e.g., in the "neat method"). In each case, the heated process fluid 203 coupled to and in contact with the sample fluid 255 provides the fluid mechanism accomplishing the aspiration and/or dispensing of the sample fluid 255.

Figure 5A:
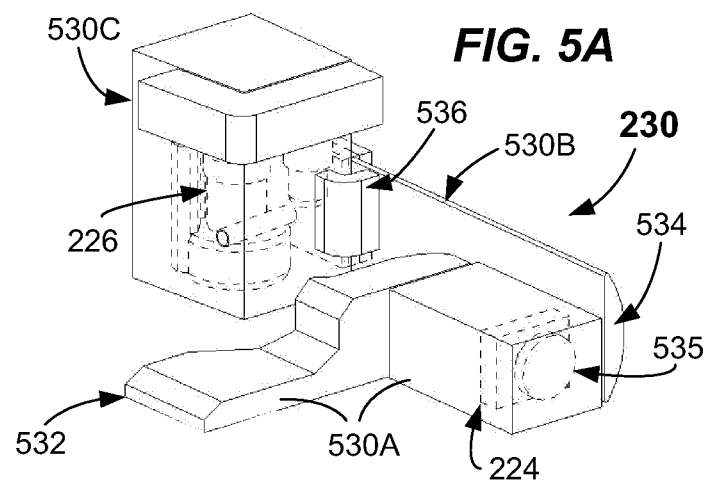
FIGS. 5A and 5B are perspective view illustrations of an exemplary shroud system according to embodiments of the present invention.
Figure 5B:
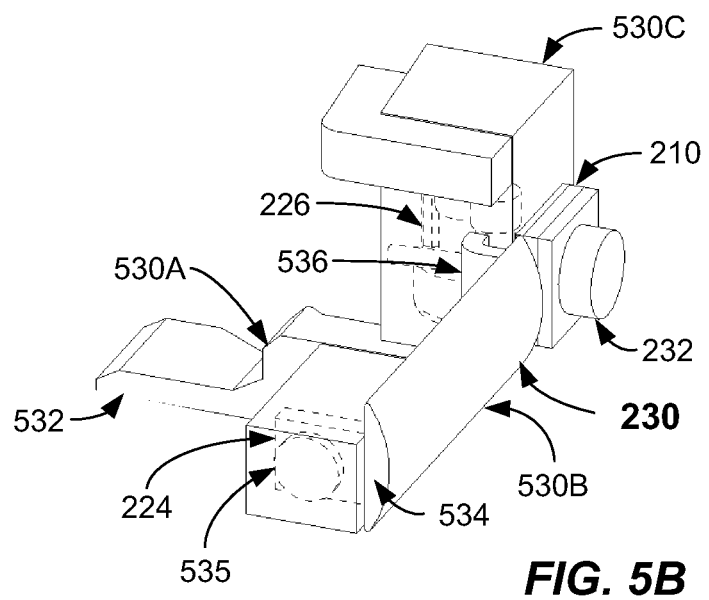

In FIGS. 5A and 5B, shrouding of the one or more heat-generating system components is illustrated. In the depicted embodiment, the refrigerator unit 224 and vacuum pump 226 are shown at least partially surrounded by the shroud system 230. Shroud system 230 may be made up of shroud subsystems 530A, 530B, and 530C. For example, the refrigerator unit 224 may be housed within shroud subsystem 530A including an inlet 532 and an outlet 534. An auxiliary fan 535 may be provided to draw air across the refrigerator unit 224. The second subsystem 530B includes a rear duct that may control and confine the flow of air to the second heat exchanger 210. Fan 232 is shown installed on a downstream side of the second heat exchanger 210. A third shroud subsystem 530C at least partially surrounds the vacuum pump 226 (and possibly other system components) and a duct outlet 536 of the rear duct 530B flows into the third shroud subsystem 530C. Together, the shroud system 230 provides controlled airflow over the one or more heat-generating system components (e.g., the refrigerator unit 224, vacuum pump 226, etc.) and to the second heat exchanger 210, which then heats the process fluid 203 flowing in the first path 204 (See FIG. 2). A more detailed view of a heat exchanger assembly 810 including a first and second heat exchanger is described with reference to FIGS. 8 and 10.

Figure 6:
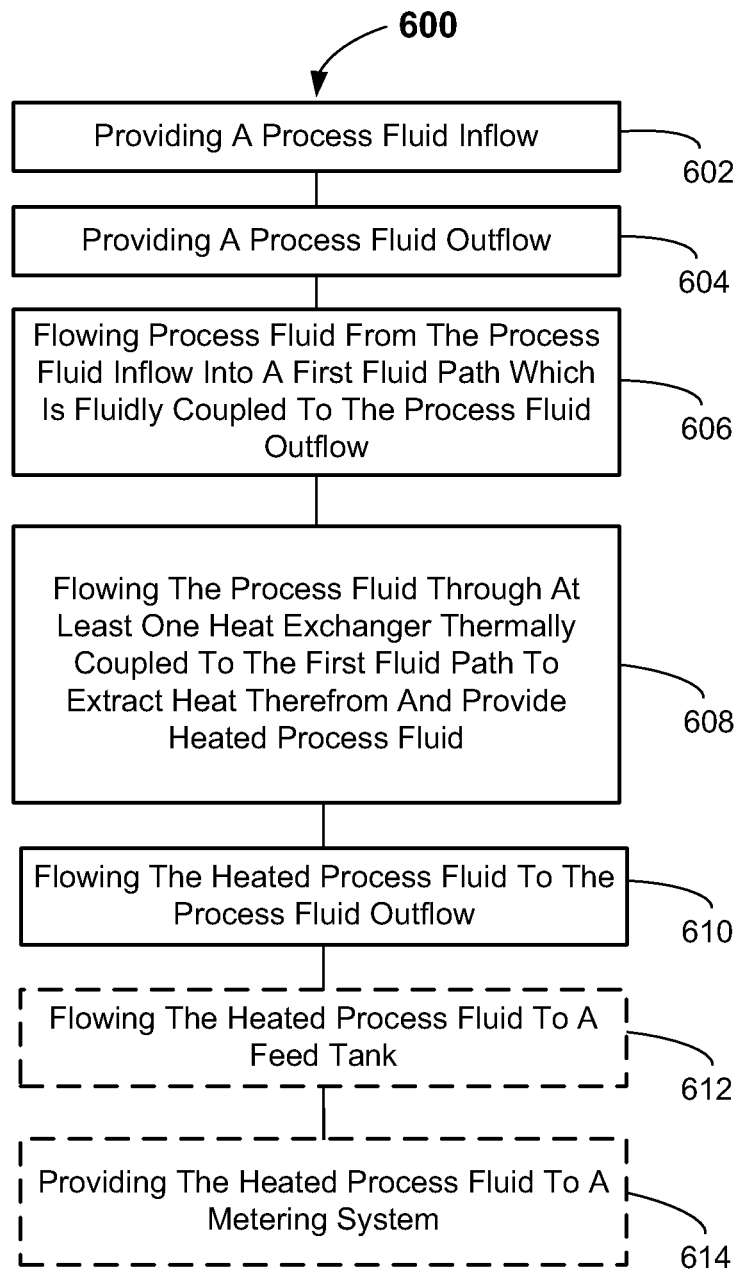
FIG. 6 is a flowchart illustrating a method of providing a temperature-controlled process fluid in an instrument according to embodiments of the present invention.

According to a first aspect, a method of providing a temperature-controlled process fluid in an instrument according to some embodiments will now be described in more detail with reference to FIG. 6. The method 600 includes, in 602, providing a process fluid inflow (e.g., process fluid inflow 202) of the instrument, and, in 604, providing a process fluid outflow (e.g., process fluid outflow 205) of the instrument. In 606 of the method, a process fluid (e.g., process fluid 203, such as water) flows from the process fluid inflow into a first fluid path (e.g., first fluid path 204) that is fluidly coupled to the process fluid outflow. The method includes, in 608, flowing the process fluid through at least one heat exchanger (e.g., $1^{st}$ heat exchanger 208 and/or $2^{nd}$ heat exchanger 210) thermally coupled to the first fluid path to extract heat from one or more heat-generating components (e.g., refrigerator unit 224, vacuum pump 226, other 228) of the instrument and provide a heated process fluid in path segment 204B. This is followed by flowing the heated process fluid to the process fluid outflow in 610. In 612, the heated process fluid may optionally then flow to a feed tank (e.g. feed tank 222), and the heated process fluid may optionally thereafter be provided to a fluid metering system (e.g., 234) in 614.

In some embodiments, the at least one heat exchanger may be a heat exchanger that is thermally coupled (e.g., through convention, etc.) to one or more heat-generating system components to extract heat from the one or more system components. The heated process fluid optionally provided to the metering system (e.g., 234) may flow through a metering pump (e.g., metering pump 238) of the fluid metering system and into a metering line (e.g., metering line 246). The method 600 may further include a step of flowing the heated process fluid through the metering line and to a probe (e.g., a sample probe). In some embodiments, the heated process fluid may be dispensed from a probe (e.g., a sample probe 248) into a sample container (e.g., container 250). According to some embodiments, an operating temperature of the heated process fluid in the feed tank (e.g., 222) is controlled to be about +/−20%, or even about +/−15%, or even about +/−10% from a nominal operating temperature as measured in ° C.

Figure 7:
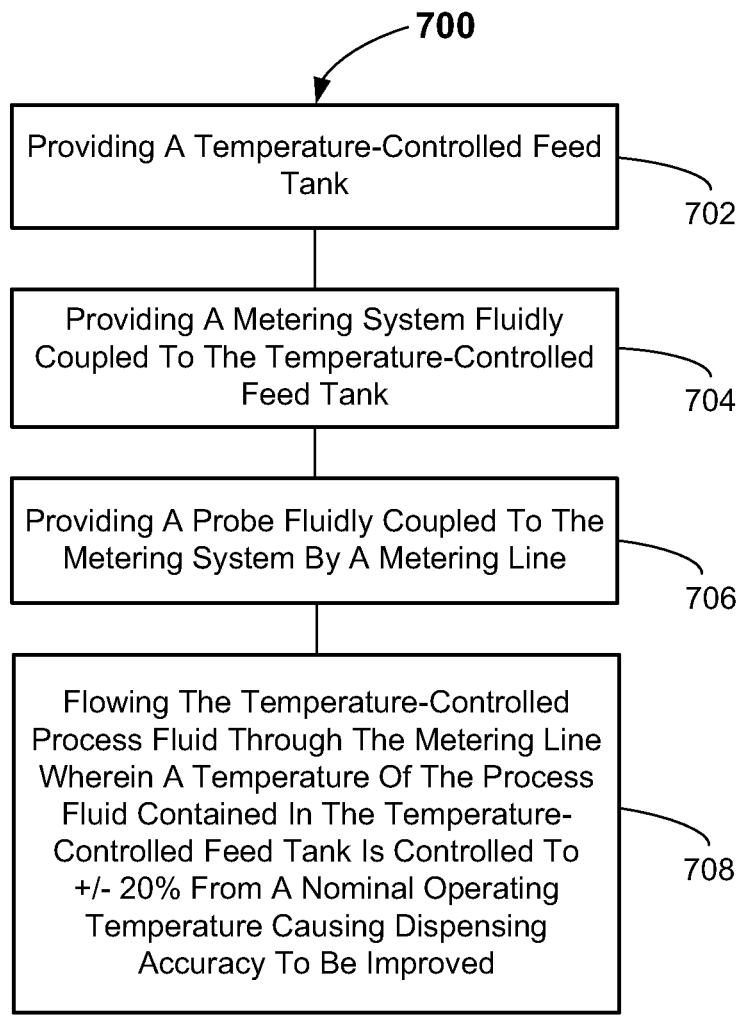
FIG. 7 is a flowchart illustrating another method of providing a temperature-controlled process fluid according to embodiments of the present invention.

According to another method aspect, a method of providing a temperature-controlled process fluid according to some embodiments will now be described with reference to FIG. 7. The method 700 includes, in 702, providing a temperature-controlled feed tank (e.g., feed tank 222), providing a fluid metering system (e.g., metering system 234) fluidly coupled to the temperature-controlled feed tank in 704, and providing a probe (e.g., probe 248) fluidly coupled to the fluid metering system by a metering line (e.g., metering line 246) in 706. The method 700 further includes, in 708, flowing the temperature-controlled process fluid through the metering line wherein a temperature of the process fluid contained in the temperature-controlled feed tank is controlled to about +/−20%, about +/−15%, or even about +/—10% from a nominal operating temperature (as measured in ° C.) whereby one of aspiration accuracy, dispensing accuracy or both may be improved.

It was discovered by the inventors herein that a 1° C. average change in a temperature of 3 mL of process fluid (e.g., water) in the metering line may produce a 0.7 μL change in a volume thereof. Accordingly, precise control of the temperature of the process fluid in the metering line (e.g., 246) is important for precise fluid (e.g., liquid) metering. This may be achieved by providing a relatively constant temperature of the heated process fluid in the feed tank 222. This relatively constant temperature of the process fluid 203 may be provided from the process fluid outflow 205.

In addition to providing a relatively constant temperature process fluid in the feed tank 222, it may be important to provide thermal shields and/or insulation around the feed tank 222 to shield and/or insulate the feed tank 222 from heat generated elsewhere in the process fluid temperature control system 200. Likewise, thermal shields and/or insulation may be provided around the metering pump 238, distribution manifold 244, and metering line 246 to shield and/or insulate them from heat generated elsewhere in the system 200. Furthermore, a temperature of the process fluid 203 (e.g., water) provided and entering at the process fluid inflow 202 may be relatively controlled within certain limits, such as by the use of a hot and cold blended process fluid being initially provided to the system 200 at the inlet 202.

Figure 3:
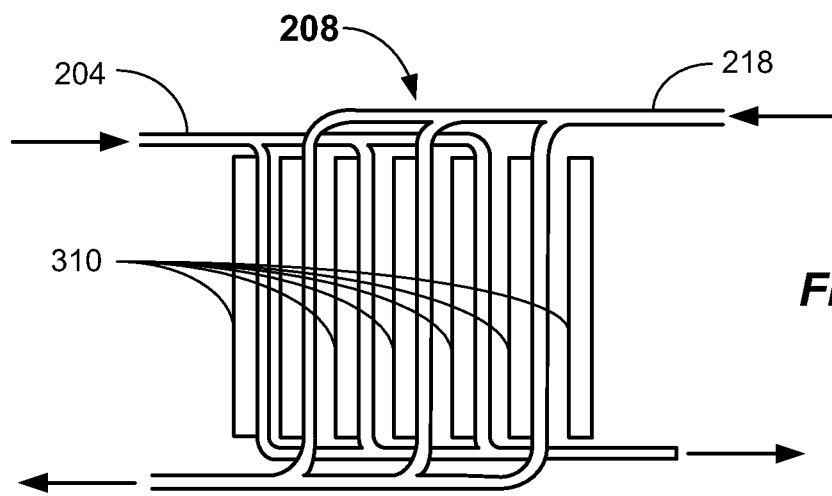
FIG. 3 is a side view illustration of an exemplary liquid-to-liquid heat exchanger according to embodiments of the present invention.
Figure 8:
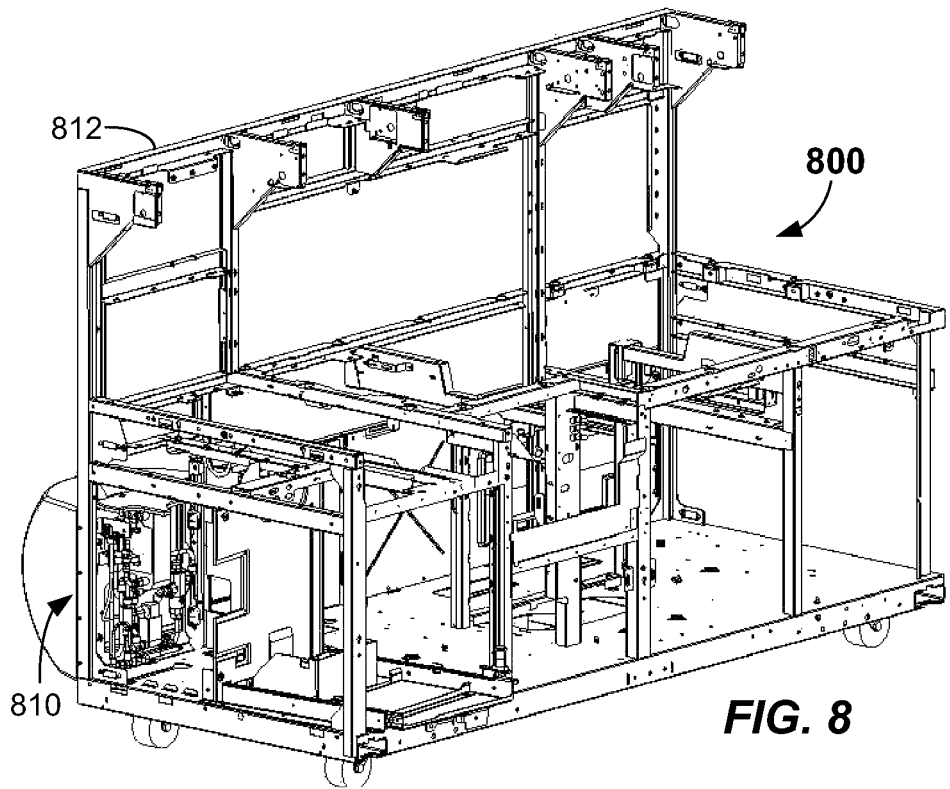
FIG. 8 is a front perspective view illustrating portions of a fluid temperature control system mounted in a frame of a clinical analyzer instrument according to embodiments of the present invention.
Figure 9:
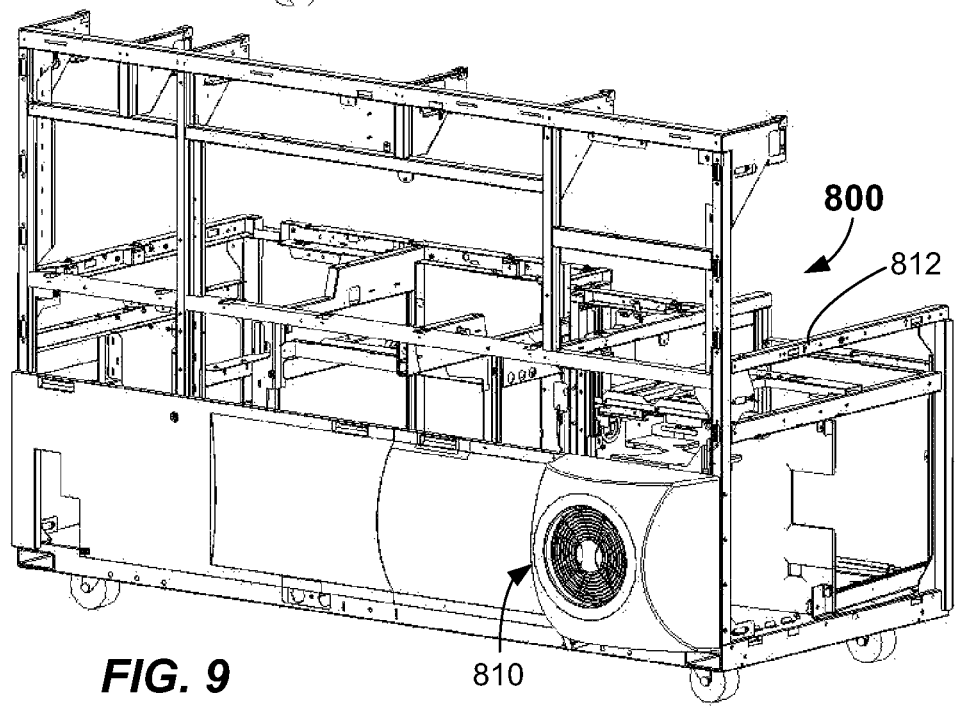
FIG. 9 is a rear perspective view illustrating portions of the fluid temperature control system of FIG. 8.
Figure 10:
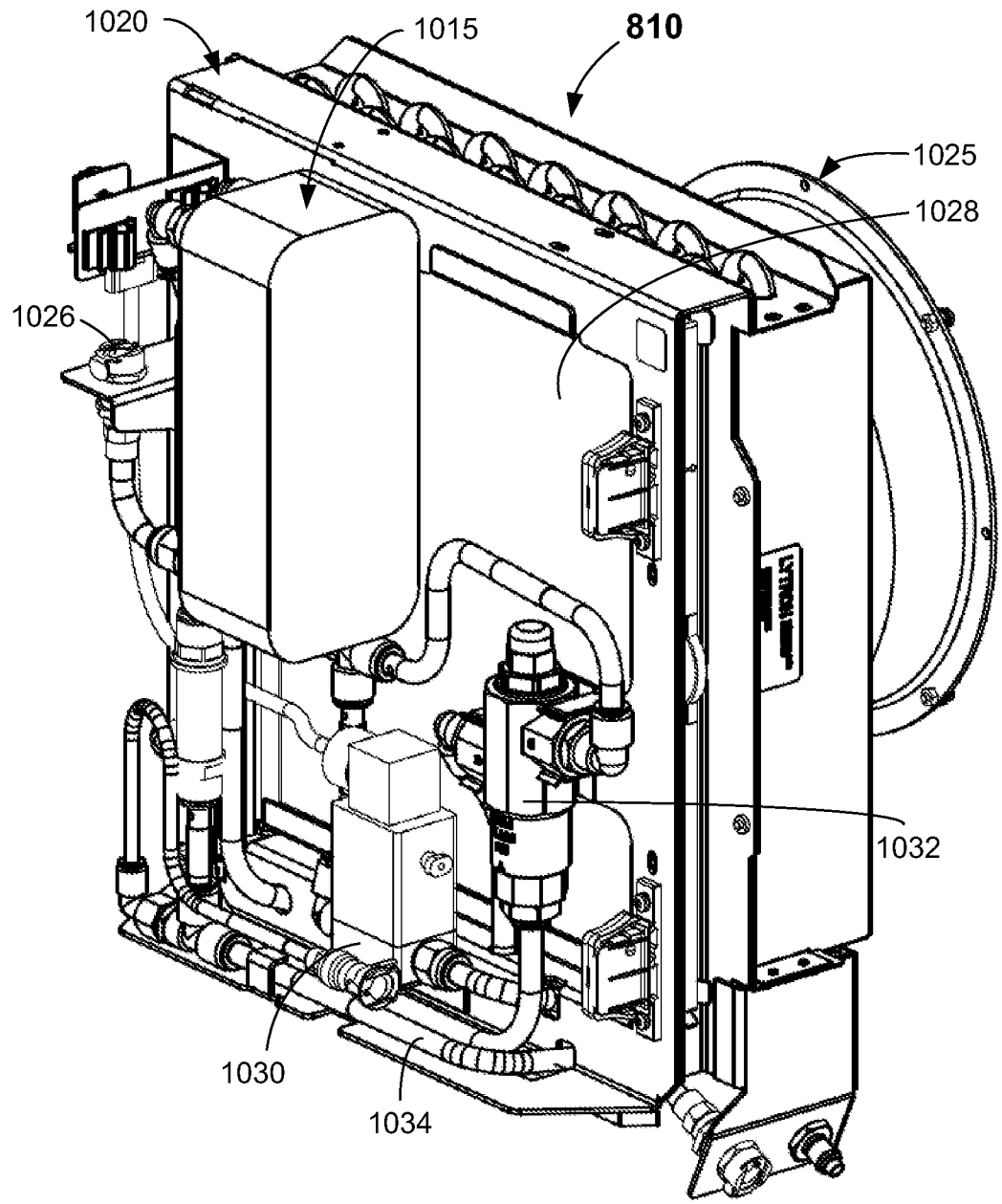
FIG. 10 is a perspective view illustrating a heat exchanger assembly of the fluid temperature control system of FIG. 8.
Figure 11:
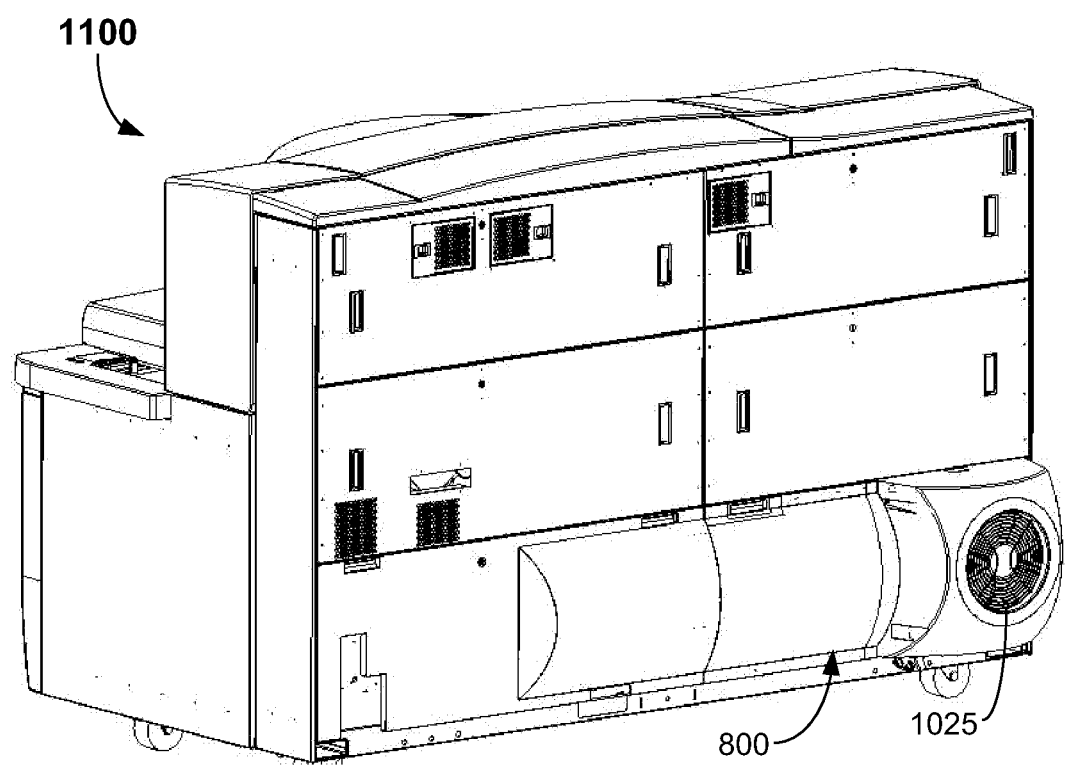
FIG. 11 is a rear perspective view illustrating the clinical analyzer instrument including the fluid temperature control system of FIG. 8.

FIGS. 8 and 9 illustrate front and rear perspective views of portions of a process fluid temperature control system 800 that is mounted to a frame 812 of a clinical analyzer instrument 1100 (FIG. 11). The process fluid temperature control system 800 may include a heat exchanger assembly 810. As shown in FIG. 10, the heat exchanger assembly 810 may include a first heat exchanger 1015, a second heat exchanger 1020, and a fan unit 1025. The first heat exchanger 1015 is optional, but may increase the overall efficiency of the system 800. The first heat exchanger 1015 may be a liquid-to-liquid heat exchanger (e.g., a plate heat exchanger) such as shown in FIG. 3, whereas the second heat exchanger 1020 may be an air-to-liquid heat exchanger (e.g., a fin-and-tube heat exchanger) as shown in FIG. 4. An air filter 1028 may be mounted upstream of the second heat exchanger 1020. The first heat exchanger 1015 may be coupled to the fluid flow inlet 1026. A flow solenoid 1030 may be used to control the flow of process fluid 203 into the heat exchanger assembly 810. Likewise, a blend valve 1032 may be used to blend heated process fluid flowing in the first fluid path 1034 with inflow fluid so that process fluid of a desired controlled or preset temperature is provided to the feed tank 222 (FIG. 2) in the process fluid outflow from the heat exchanger assembly 810. The heat exchanger assembly 810 provides a compact assembly arrangement of the first and second heat exchangers 1015, 1020.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus or methods disclosed, but, to the contrary, the intention is to cover all modifications, equivalents, and alternatives falling within the spirit and scope of the invention.

What is claimed is:

1. A process fluid temperature control system, comprising:
a process fluid inflow adapted to provide a process fluid;
a process fluid outflow;
a first fluid path fluidly coupled to the process fluid inflow and the process fluid outflow;
at least one heat exchanger coupled to the first fluid path and adapted to extract heat generated by a component of an instrument and heat the process fluid;
a blend valve fluidly and operatively coupled to the process fluid inflow and to the first fluid path and configured to control a temperature of the process fluid in the process fluid outflow by blending unheated process fluid from the process fluid inflow with heated process fluid in the first fluid path from the at least one heat exchanger;
a feed tank fluidly coupled to the process fluid outflow; and
a metering system fluidly coupled to the feed tank.

2. The fluid temperature control system of claim 1, wherein the at least one heat exchanger further comprises a first heat exchanger and a second heat exchanger, each of the first and second heat exchangers being thermally coupled to the first fluid path.

3. The fluid temperature control system of claim 1, further comprising a fluid purification system coupled to the process fluid outflow.

4. The fluid temperature control system of claim 3, further comprising a second fluid path fluidly coupled to an outflow from the fluid purification system and to a first heat exchanger comprising the at least one heat exchanger.

5. The fluid temperature control system of claim 4, wherein the first heat exchanger functions to extract heat from the second fluid path and transfer a portion of the heat to the first fluid path.

6. The fluid temperature control system of claim 1, wherein the process fluid inflow is coupled to the first fluid path by a solenoid valve.

7. The fluid temperature control system of claim 1, wherein the blend valve includes a temperature sensor to control a temperature of the process fluid in the process fluid outflow.

8. The fluid temperature control system of claim 1, wherein the at least one heat exchanger further comprises a first heat exchanger and a second heat exchanger thermally coupled to the first fluid path, wherein the outflow of the first heat exchanger is provided to an inflow of the second heat exchanger.

9. The fluid temperature control system of claim 1, wherein the at least one heat exchanger is adapted to extract heat from at least one heat-generating component of the instrument.

10. The fluid temperature control system of claim 9, wherein the at least one heat exchanger is adapted to extract heat from a vacuum pump of the instrument.

11. The fluid temperature control system of claim 9, wherein the at least one heat exchanger is adapted to extract heat from a refrigerator unit of the instrument.

12. A method of providing a temperature-controlled process fluid, comprising:
providing a process fluid inflow;
providing a process fluid outflow;
flowing process fluid from the process fluid inflow into a first fluid path that is fluidly coupled to the process fluid outflow;
flowing the process fluid through at least one heat exchanger thermally coupled to the first fluid path to extract heat from one or more heat-generating components of an instrument and provide a heated process fluid;
blending unheated process fluid from the process fluid inflow with the heated process fluid from the at least one heat exchanger to control a temperature of the heated process fluid;
flowing the heated process fluid to the process fluid outflow; and
flowing the heated process fluid through a pump of a metering system and into a metering line.

13. The method of claim 12, further comprising thermally coupling the at least one heat exchanger to the one or more heat-generating components of the instrument to extract heat from the one or more components.

14. The method of claim 12, wherein the at least one heat exchanger comprises a first heat exchanger and a second heat exchanger, and further comprising flowing the process fluid through the first heat exchanger and the second heat exchanger, the second heat exchanger being thermally coupled to the one or more heat-generating components of the instrument to extract heat from the one or more components.

15. The method of claim 12, further comprising flowing the heated process fluid to a feed tank.

16. The method of claim 12, further comprising flowing the heated process fluid in the metering line toward a probe.

17. The method of claim 16, further comprising dispensing the heated process fluid from the probe into a sample container.

18. The method of claim 12, further comprising controlling an operating temperature of the heated process fluid in the process fluid outflow to be +/−20% from a nominal operating temperature (as measured in ° C.).

19. The method of claim 12, wherein the heated process fluid is fluidly coupled to a reagent contained in a probe.

20. A method of claim 12, comprising:
providing a temperature-controlled feed tank;
providing the metering system fluidly coupled to the temperature-controlled feed tank;
providing a probe fluidly coupled to the metering system by the metering line; and
flowing the heated process fluid through the metering line, wherein a temperature of the heated process fluid contained in the temperature-controlled feed tank is controlled to about +/−20% (in ° C.) from a nominal operating temperature whereby aspiration accuracy, dispensing accuracy, or both are improved.

21. A method of providing a temperature-controlled process fluid, comprising:
providing a process fluid inflow;
providing a process fluid outflow;
flowing process fluid from the process fluid inflow into a first fluid path that is fluidly coupled to the process fluid outflow;
flowing the process fluid through at least one heat exchanger thermally coupled to the first fluid path to extract heat from one or more heat-generating components of an instrument and provide a heated process fluid;
blending unheated process fluid from the process fluid inflow with the heated process fluid from the at least one heat exchanger to control a temperature of the heated process fluid;
flowing the heated process fluid to the process fluid outflow; and
wherein the heated process fluid is fluidly coupled to a bio-fluid sample contained in a probe.

22. A fluid temperature control apparatus, comprising:
a process fluid inflow;
a process fluid outflow;
a fluid purifier coupled to the process fluid outflow;
a first fluid path fluidly coupled to the process fluid inflow and process fluid outflow;
a first heat exchanger thermally coupled to the first fluid path;
a second heat exchanger thermally coupled to the first fluid path and adapted to extract heat from at least one heat-generating component of an instrument;
a second fluid path fluidly coupled to an outflow of the fluid purifier and the first heat exchanger;
a blend valve fluidly coupled to the process fluid inflow and to the first fluid path and configured to control a temperature of the process fluid in the process fluid outflow by blending unheated process fluid from the process fluid inflow with heated process fluid in the first fluid path from the second heat exchanger;
a feed tank fluidly coupled to the process fluid outflow; and
a metering system fluidly coupled to the feed tank.

* * * * *